(12) United States Patent
Vincent

(10) Patent No.: US 8,716,444 B2
(45) Date of Patent: May 6, 2014

(54) METHOD AND APPARATUS FOR PREDICTING SUSCEPTIBILITY TO A DEVELOPMENTAL DISORDER

(75) Inventor: John B. Vincent, Toronto (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 13/258,929

(22) PCT Filed: Mar. 26, 2010

(86) PCT No.: PCT/CA2010/000448
§ 371 (c)(1),
(2), (4) Date: Nov. 17, 2011

(87) PCT Pub. No.: WO2010/108275
PCT Pub. Date: Sep. 30, 2010

(65) Prior Publication Data
US 2012/0065083 A1    Mar. 15, 2012

Related U.S. Application Data

(60) Provisional application No. 61/164,200, filed on Mar. 27, 2009.

(51) Int. Cl.
*C07K 1/00* (2006.01)
*C12Q 1/68* (2006.01)

(52) U.S. Cl.
USPC ............................................ 530/350; 435/6.1

(58) Field of Classification Search
None
See application file for complete search history.

(56) References Cited

U.S. PATENT DOCUMENTS

2007/0054278 A1    3/2007    Cargill
2007/0281896 A1    12/2007   Morris et al.

OTHER PUBLICATIONS

Hu et al., The Journal of Biological Chemistry, 2005, vol. 280, pp. 29233-29241.*
GenBank Accession No. DA099363. Brace 3 *Homo sapiens* cDNA clone BRACE3010766 5-, mRNA sequence, Jan. 2008.
GenBank Accession No. BAB67775. KIAA1882 protein [*Homo sapiens*], Sep. 2001.
GenBank Accession No. BAG10171. NIK and IKK (beta) binding protein [synthetic construct], Oct. 2008.
International Search Report, PCT/CA2010/000448, mailed Jun. 23, 2010.
Ganeshwaran et al., "A Truncating Mutation of TRAPPC9 is Associated with Autosomal-Recessive Intellectual Disability and Postnatal Microcephaly", American Journal of Human Genetics, vol. 85, No. 6, pp. 897-902 (2009).
Mir et al., "Identification of Mutations in TRAPPC9, which Encodes the NIK- and IKK-β-Binding Protein, in Nonsyndromic Autosomal-Recessive Mental Retardation", American Journal of Human Genetics, vol. 85, No. 6, pp. 909-915 (2009).
Phillippe et al., Combination of Linkage Mapping and Microarray-Expression Analysis Identifies NF-κB Signaling Defect as a Cause of Autosomal-Recessive Mental Retardation, American Journal of Human Genetics, vol. 85, No. 6, pp. 903-908 (2009).

* cited by examiner

*Primary Examiner* — Anne Gussow
*Assistant Examiner* — Mindy G Brown
(74) *Attorney, Agent, or Firm* — Winston & Strawn LLP

(57) ABSTRACT

The present invention provides a method of screening a subject for mutations in the TRAPPC9 gene that are associated with developmental disabilities. The present invention also provides proteins that are associated with developmental disabilities including a truncation of NIBP. Also provided are nucleotide sequences encoding such proteins and methods of screening subjects to identify nucleotide sequences or proteins associated with developmental disabilities.

4 Claims, 5 Drawing Sheets

SEQ ID NO. 1:

```
   1 aaagtcggga gtgccatggt gccagctggg gatcaagacc gcgcgccaca caggggaag
  61 ccggcccagg ctggggctcg cacctcacgt gcctcccggg ccctgcgatc ctggaggcgc
 121 tcccaggccg cgcgcgccac ggtcacccac ccacgtgggg ggcacgaccg tgggagtcac
 181 gggggtacc gtgagggtca caggggtgc cgcagggatc cacagtgggc ttccgcgggg
 241 cctccacccc tgagcttcac agaggaagtg aaatttgagc tgcgcgccct gaaggactgg
 301 gacttcaaaa tgagcgtccc tgactacatg cagtgtgctg aggaccacca gacgctgctc
 361 gtggtggtcc agcctgtggg catcgtctcc gaggagaact tcttcaggat ctataagagg
 421 atttgctctg tgagtcagat cagcgtgcgg gactcccagc gagtcctcta catccgctac
 481 aggcaccact acccacccga gaacaacgag tggggtgact tccagaccca ccgcaaagtc
 541 gtgggcctca tcaccatcac agactgcttc tcggccaagg actggccaca gacctttgag
 601 aagttccacg tgcagaagga gatctacggc tccacactgt atgactcccg gctctttgtc
 661 ttcgggctgc agggggagat cgtggagcag ccgcgcaccg acgtggcttt ctaccccaac
 721 tacgaggact gccagacggt ggagaagaga atcgaggact tcatcgagtc actgttcatc
 781 gtgctggagt ccaagcgtct ggacagagcc acagacaagt ctggggataa gatcccccct
 841 ctctgtgtcc cgtttgagaa aaaggacttt gtaggactgg acacagacag cagacattac
 901 aagaagcggt gccaaggccg catgcggaag cacgtggggg acctgtgcct gcaggcaggg
 961 atgctgcagg actccctggt gcattaccac atgtcggtgg agctgctgcg ttctgtgaat
1021 gactttctgt ggcttggagc tgccctggaa ggattgtgtt cagcttctgt catctatcac
1081 tatcctggtg gaactggtgg gaagagtgga gctcggaggt tccagggcag cacccttcct
1141 gctgaagcag ccaatagaca ccggccaggg gcacaggaag ttctcattga tccaggtgcc
1201 ctcaccacca atggcatcaa ccctgacacc agtactgaga tcggacgtgc taagaactgc
1261 cttagccctg aagacataat tgacaagtat aaagaggcga tttcctatta cagcaagtat
1321 aagaatgcgg gagtgattga gttggaagcg tgcatcaagg ctgtacgtgt ccttgcaatt
1381 cagaaacgga gcatggaagc atcagaattt cttcagaatg cagtttacat taaccttcga
1441 cagctttctg aggaagagaa aattcagcgc tacagcatcc tctccgagct ctatgagctg
1501 atcggcttcc atcgcaagtc tgcgttcttc aagcgcgtgg ccgccatgca gtgcgtggcc
1561 ccaagcatcg cggagcctgg gtggagggcc tgctacaaac tcctcctgga aacgctgccc
1621 ggctacagtc tgtcgctgga tcccaaagat ttcagcagag gcacgcacag aggctgggct
1681 gcggtccaga tgcgtttgct ccatgaattg gtctacgcct cccgaaggat ggggaaccct
1741 gccctctctg tcagacacct gtccttcctt ctacagacca tgctggactt cttgtcggat
1801 caggaaaaga aagatgtggc ccaaagccta gagaactata cgtccaagtg tcctgggacc
1861 atggagccca tcgccctccc tggcggcctc accctgccac cggtgccctt caccaagctt
1921 cccgtcgtca ggcatgtgaa actattgaac cttcctgcta gcctccggcc acacaaaatg
1981 aaaagcttgc tgggtcagaa cgtgtcaacc aaaagtcctt tcatctattc accaattatc
2041 gcacacaacc gtggagaaga gcggaacaag aaaatagatt ccagtgggt tcaaggagat
2101 gtgtgtgaag ttcagctgat ggtatataac ccaatgccgt ttgaacttcg agttgaaaac
2161 atgggctgc tcaccagcgg agtggagttc gagtctctcc ctgcggcgct ttctcttccg
2221 gctgaatctg gtctgtaccc agtgacgctc gtcgggtcc cgcagacgac tggaacgatt
2281 actgtgaacg gttaccatac cacggtcttc ggtgtgttca gtgactgttt gctggataac
2341 ctgccggaaa taaaaccag tggctccaca gtggaagtca ttcccgcgtt gccaagactg
2401 cagatcagca cctctctgcc cagatctgca cattcattgc aaccttcttc tggtgatgaa
2461 atatctacta atgtatctgt ccagctttac aatggagaaa gtcagcaact aatcattaaa
2521 ttggaaaata ttggaatgga accattggag aaactggagg tcacctcgaa agttctcacc
2581 actaaagaaa aattgtatgg cgacttcttg agctggaagc tagaggaaac ccttgcccag
2641 tcccctttgc agcctggaa ggtggccacg ttcacaatca acatcaaagt gaagctggat
2701 ttctcctgcc aggagaatct cctgcaggat ctcagtgatg atggaagcag tgtgagtggc
2761 tttccctgt ccagtccttt tcggcaggtc gttcggccc gagtggaggg caaacctgtg
2821 aacccacccg agagcaacaa agcaggcgac tacagccacg tgaagaccct ggaagctgtc
2881 ctgaatttca aatactctgg aggcccgggc cacactgaag gatattacag gaatctctcc
2941 ctggggctgc atgtagaagt cgagccgtct gtattttca cccgagtcag caccctccca
3001 gcaaccagta cccggcagtg tcacctgctc ctggatgtct tcaactccac cgagcatgag
3061 ctgaccgtca gcaccaggag cagcgaggca ctcatcctgc acgccggcga gtgccagcga
3121 atggctattc aagtggacaa gttcaacttt gagagttcc cggagtcccc tggggagaag
3181 gggcaattg caaaccccaa gcagctggag gaagagcggc gggaagcccg aggcctggag
3241 atccacagca gctgggcat ctgctggaga atcccctccc tgaagcgcag tggcgaggcg
3301 agtgtggaag gactcctgaa ccagctcgtc ctggagcacc tgcagctggc gcctctgcag
```

FIG. 1

```
3361 tgggatgtgc tggtggacgg acagccatgt gaccgcgagg ctgtggcggc ctgccaggtg
3421 ggcgaccccg tgcgcctgga ggtgcggctg accaaccgga gcccgcgcag cgtagggccc
3481 ttcgccctca ctgtggtccc cttccaggac caccagaacg gcgtgcacaa ctacgacctg
3541 cacgacaccg tctccttcgt gggctccagc accttctacc tcgacgcggt gcagccgtcc
3601 ggccagtcgg cctgcctcgg ggccctcctc ttcctctaca cgggagactt cttcctccac
3661 atccggttcc acgaggacag caccagcaag gagctgccac cctcttggtt ctgcctgccc
3721 agtgtgcacg tgtgtgccct ggaggcgcag gcctgagccc gcctacttcc gtccctcttt
3781 ctgcagggcc agaggtgacc ctgcctggcc tcccacaccc cctgcaatga gcaaggcctt
3841 cactgcagcc ccatctcctc ctcctccccc agacccctcc cagccctctc ctcctgttcc
3901 tcctgtagca tctttgctgg gctacgcaga agccccggac atggcagccc caccccatgc
3961 cacgccccctt cctacactgt tccctggacc atacacaggc tgaagcagag gaaatcccaa
4021 agcgggtgcc catccagccc aggtcccagg atccctgcac ccatttctgt gacctggggc
4081 cccagccgtg ctgtgctgct catcccagca gagggacctc cctcgtccag cgacttccct
4141 ttggccatag aaagaaatgg tgagcatgag actgggcaca gcctgagggc gtgggcagct
4201 tcccaccctc cctgggcctt ggaatccccc aaggctggtt ttcttcctgg agacccccat
4261 gggcaacttg gcaggagaga tggtgccgta ggaggtcgtg gatggttgat gccaagagag
4321 gccctccacc cgtggtgggc aaatgtccag gcctgggctg cagcccagg gctgtttctg
4381 ggtgctccct ggccccaggg tggcgtctgg ttaccatggc tgtgtgtgtc catgtctgca
4441 agcagttctt caataaatgg cctgcctccc cc
```

FIG.1 (cont'd)

SEQ ID NO. 2:

```
   1 mvpagdqdra phrgkpaqag artsrasral rswrrsqaar atvthprggh drgshggyre
  61 ghrgcrrdpq wasagpppls fteevkfelr alkdwdfkms vpdymqcaed hqtllvvvqp
 121 vgivseenff riykricsvs qisvrdsqrv lyiryrhhyp pennewgdfq thrkvvglit
 181 itdcfsakdw pqtfekfhvq keiygstlyd srlfvfglqg eiveqprtdv afypnyedcq
 241 tvekriedfi eslfivlesk rldratdksg dkipllcvpf ekkdfvgldt dsrhykkrcq
 301 grmrkhvgdl clqagmlqds lvhyhmsvel lrsvndflwl gaaleglcsa sviyhypggt
 361 ggksgarrfq gstlpaeaan rhrpgaqevl idpgalttng inpdtsteig raknclsped
 421 iidkykeais yyskyknagv ieleacikav rvlaiqkrsm easeflqnav yinlrqlsee
 481 ekiqrysils elyeligfhr ksaffkrvaa mqcvapsiae pgwracykll letlpgysls
 541 ldpkdfsrgt hrgwaavqmr llhelvyasr rmgnpalsvr hlsfllqtml dflsdqekkd
 601 vaqslenyts kcpgtmepia lpggltlppv pftklpvvrh vkllnlpasl rphkmksllg
 661 qnvstkspfi yspiiahnrg eernkkidfq wvqgdvcevq lmvynpmpfe lrvenmgllt
 721 sgvefeslpa alslpaesgl ypvtlvgvpq ttgtitvngy httvfgvfsd clldnlpgik
 781 tsgstvevip alprlqists lprsahslqp ssgdeistnv svqlyngesq qliiklenig
 841 mepleklevt skvltttkekl ygdflswkle etlaqfplqp gkvatftini kvkldfscqe
 901 nllqdlsddg isvsgfplss pfrqvvrprv egkpvnppes nkagdyshvk tleavlnfky
 961 sggpghtegy yrnlslglhv evepsvfftr vstlpatstr qchllldvfn steheltvst
1021 rssealilha gecqrmaiqv dkfnfesfpe spgekgqfan pkqleeerre argleihskl
1081 gicwripslk rsgeasvegl lnqlvlehlq laplqwdvlv dgqpcdreav aacqvgdpvr
1141 levrltnrsp rsvgpfaltv vpfqdhqngv hnydlhdtvs fvgsstfyld avqpsgqsac
1201 lgallflytg dfflhirfhe dstskelpps wfclpsvhvc aleaqa
```

FIG. 2

SEQ ID NO. 3:

```
   1 aaagtcggga gtgccatggt gccagctggg gatcaagacc gcgcgccaca caggggggaag
  61 ccggcccagg ctggggctcg cacctcacgt gcctcccggg ccctgcgatc ctggaggcgc
 121 tcccaggccg cgcgcgccac ggtcacccac ccacgtgggg ggcacgaccg tgggagtcac
 181 gggggggtacc gtgagggtca caggggggtgc cgcagggatc cacagtgggc ttccgcgggg
 241 cctccacccg tgagcttcac agaggaagtg aaatttgagc tgcgcgccct gaaggactgg
 301 gacttcaaaa tgagcgtccc tgactacatg cagtgtgctg aggaccacca gacgctgctc
 361 gtggtggtcc agcctgtggg catcgtctcc gaggagaact tcttcaggat ctataagagg
 421 atttgctctg tgagtcagat cagcgtgcgg gactcccagc gagtcctcta catccgctac
 481 aggcaccact acccacccga gaacaacgag tggggtgact tccagaccca ccgcaaagtc
 541 gtgggcctca tcaccatcac agactgcttc tcggccaagg actggccaca gacctttgag
 601 aagttccacg tgcagaagga gatctacggc tccacactgt atgactcccg gctctttgtc
 661 ttcgggctgc aggggggagat cgtggagcag ccgcgcaccg acgtggcttt ctaccccaac
 721 tacgaggact gccagacggt ggagaagaga atcgaggact tcatcgagtc actgttcatc
 781 gtgctggagt ccaagcgtct ggacagagcc acagacaagt ctggggataa gatccccctt
 841 ctctgtgtcc cgtttgagaa aaaggacttt gtaggactgg acacagacag cagacattac
 901 aagaagcggt gccaaggccg catgcggaag cacgtggggg acctgtgcct gcaggcaggg
 961 atgctgcagg actccctggt gcattaccac atgtcggtgg agctgctgcg ttctgtgaat
1021 gactttctgt ggcttggagc tgccctggaa ggattgtgtt cagcttctgt catctatcac
1081 tatcctggtg gaactggtgg gaagagtgga gctcggaggt tccagggcag caccccttcct
1141 gctgaagcag ccaatagaca ccggccaggg gcacaggaag ttctcattga tccaggtgcc
1201 ctcaccacca atggcatcaa ccctgacacc agtactgaga tcggacgtgc taagaactgc
1261 cttagccctg aagacataat tgacaagtat aaagaggcga tttcctatta cagcaagtat
1321 aagaatgcgg gagtgattga gttggaagcg tgcatcaagg ctgtacgtgt ccttgcaatt
1381 cagaaacgga gcatggaagc atcagaattt cttcagaatg cagtttacat taacctttga
1441 cagctttctg aggaagagaa aattcagcgc tacagcatcc tctccgagct ctatgagctg
1501 atcggcttcc atcgcaagtc tgcgttcttc aagcgcgtgg ccgccatgca gtgcgtggcc
1561 ccaagcatcg cggagcctgg gtggagggcc tgctacaaac tcctcctgga aacgctgccc
1621 ggctacagtc tgtcgctgaa tcccaaagat ttcagcagag gcacgcacag aggctgggct
1681 gcggtccaga tgcgtttgct ccatgaattg gtctacgcct cccgaaggat ggggaaccct
1741 gccctctctg tcagacacct gtccttcctt ctacagacca tgctggactt cttgtcggat
1801 caggaaaaga aagatgtggc ccaaagccta gagaactata cgtccaagtg tcctgggacc
1861 atggagccca tcgccctccc tgcggcctc accctgccac cggtgccctt caccaagctt
1921 cccgtcgtca ggcatgtgaa actattgaac cttcctgcta gcctccggcc acacaaaatg
1981 aaaagcttgc tgggtcagaa cgtgtcaacc aaaagtcctt tcatctattc accaattatc
2041 gcacacaacc gtggagaaga gcggaacaag aaaatagatt ccagtgggt tcaaggagat
2101 gtgtgtgaag ttcagctgat ggtatataac ccaatgccgt ttgaacttcg agttgaaaac
2161 atggggctgc tcaccagcgg agtggagttc gagtctctcc ctgcggcgct ttctcttccg
2221 gctgaatctg gtctgtaccc agtgacgctc gtcggggtcc cgcagacgac tggaacgatt
2281 actgtgaacg gttaccatac cacggtcttc ggtgtgttca gtgactgttt gctggataac
2341 ctgccgggaa taaaaaccag tggctccaca gtgaagtca ttccgcgtt gccaagactg
2401 cagatcagca cctctctgcc cagatctgca cattcattgc aaccttcttc tggtgatgaa
2461 atatctacta atgtatctgt ccagctttac aatggagaaa gtcagcaact aatcattaaa
2521 ttggaaaata ttggaatgga accattggag aaactggagg tcacctcgaa agttctcacc
2581 actaaagaaa aattgtatgg cgacttcttg agctggaagc tagaggaaac ccttgcccag
2641 ttcccttttgc agcctggaa ggtggccacg ttcacaatca acatcaaagt gaagctggat
2701 ttctcctgcc aggagaatct cctgcaggat ctcagtgatg atggaatcag tgtgagtggc
2761 tttcccctgt ccagtccttt tcggcaggtc gttcggcccc gagtggaggg caaacctgtg
2821 aacccacccg agagcaacaa agcaggcgac tacagccacg tgaagaccct ggaagctgtc
2881 ctgaatttca aatactctgg aggcccggc cacactgaag gatattacag gaatctctcc
2941 ctggggctgc atgtagaagt cgagccgtct gtattttca cccgagtcag caccctccca
3001 gcaaccagta cccggcagtg tcacctgctc ctggatgtct tcaactccac cgagcatgag
3061 ctgaccgtca gcaccaggag cagcgaggca ctcatcctgc acgccggcga gtgccagcga
3121 atggctattc aagtggacaa gttcaacttt gagagtttcc cggagtcccc tggggagaag
3181 ggcaatttgc caaaccccaa gcagctggag gaagagcggc gggaagcccg aggcctggag
3241 atccacagca agctgggcat ctgctggaga atcccctccc tgaagcgcag tggcgaggcg
3301 agtgtggaag gactcctgaa ccagctcgtc ctggagcacc tgcagctggc gcctctgcag
```

FIG. 3

```
3361 tgggatgtgc tggtggacgg acagccatgt gaccgcgagg ctgtggcggc ctgccaggtg
3421 ggcgaccccg tgcgcctgga ggtgcggctg accaaccgga gcccgcgcag cgtagggccc
3481 ttcgccctca ctgtggtccc cttccaggac caccagaacg gcgtgcacaa ctacgacctg
3541 cacgacaccg tctccttcgt gggctccagc accttctacc tcgacgcggt gcagccgtcc
3601 ggccagtcgg cctgcctcgg ggccctcctc ttcctctaca cgggagactt cttcctccac
3661 atccggttcc acgaggacag caccagcaag gagctgccac cctcttggtt ctgcctgccc
3721 agtgtgcacg tgtgtgccct ggaggcgcag gcctgagccc gcctacttcc gtccctcttt
3781 ctgcagggcc agaggtgacc ctgcctggcc tcccacaccc cctgcaatga gcaaggcctt
3841 cactgcagcc ccatctcctc ctcctcccc agacccctcc cagccctctc ctcctgttcc
3901 tcctgtagca tctttgctgg gctacgcaga agccccggac atggcagccc cacccatgc
3961 cacgcccctt cctacactgt tccctggacc atacacaggc tgaagcagag gaaatcccaa
4021 agcgggtgcc catccagccc aggtcccagg atccctgcac ccatttctgt gacctggggc
4081 cccagccgtg ctgtgctgct catcccagca gagggacctc cctcgtccag cgacttccct
4141 ttggccatag aaagaaatgg tgagcatgag actgggcaca gcctgagggc gtgggcagct
4201 tcccaccctc cctgggcctt ggaatccccc aaggctggtt ttcttcctgg agaccccat
4261 gggcaacttg gcaggagaga tggtgccgta ggaggtcgtg gatggttgat gccaagagag
4321 gccctccacc cgtggtgggc aaatgtccag gcctgggctg gcagcccagg gctgtttctg
4381 ggtgctccct ggccccaggg tggcgtctgg ttaccatggc tgtgtgtgtc catgtctgca
4441 agcagttctt caataaatgg cctgcctccc cc
```

FIG.3 (cont'd)

SEQ ID NO. 4:

```
1 aatgcagttt acattaacct tXgacag
``` wherein X is C or T

FIG.4

SEQUENCE LISTING

```
<160> NUMBER OF SEQ ID NOS: 4

<210> SEQ ID NO 1
<211> LENGTH: 4472
<212> TYPE: DNA
<213> ORGANISM: Homo Sapiens

<400> SEQUENCE: 1
aaagtcggga gtgccatggt gccagctggg gatcaagacc gcgcgccaca caggggggaag      60 ccggcccagg ctggggctcg cacctcacgt gcctcccggg ccctgcgatc ctggaggcgc     120
tcccaggccg cgcgcgccac ggtcacccac ccacgtgggg ggcacgaccg tgggagtcac     180 gggggggtacc gtgagggtca caggggggtgc cgcaggggatc cacagtgggc ttccgcgggg     240
cctccacccc tgagcttcac agaggaagtg aaatttgagc tgcgcgccct gaaggactgg     300
gacttcaaaa tgagcgtccc tgactacatg cagtgtgctg aggaccacca gacgctgctc     360
gtggtggtcc agcctgtggg catcgtctcc gaggagaact tcttcaggat ctataagagg     420
atttgctctg tgagtcagat cagcgtgcgg gactcccagc gagtcctcta catccgctac     480
aggcaccact acccacccga gaacaacgag tggggtgact tccagaccca ccgcaaagtc     540
gtgggcctca tcaccatcac agactgcttc tcggccaagg actggccaca gacctttgag     600
aagttccacg tgcagaagga gatctacggc tccacactgt atgactcccg gctctttgtc     660
ttcgggctgc aggggggagat cgtggagcag ccgcgcaccg acgtggcttt ctaccccaac     720
tacgaggact gccagacggt ggagaagaga atcgaggact tcatcgagtc actgttcatc     780
gtgctggagt ccaagcgtct ggacagagcc acagacaagt ctgggggataa gatccccctt     840 ctctgtgtcc cgtttgagaa aaaggacttt gtaggactga acagacag cagacattac     900 aagaagcggt gccaaggccg catgcggaag cacgtggggg acctgtgcct gcaggcaggg     960
atgctgcagg actccctggt gcattaccac atgtcggtgg agctgctgcg ttctgtgaat    1020
gactttctgt ggcttggagc tgccctggaa ggattgtgtt cagcttctgt catctatcac    1080
tatcctggtg gaactggtgg gaagagtgga gctcggaggt tccagggcag caccctttcct    1140 gctgaagcag ccaatagaca ccggccaggg gcacaggaag ttctcattga tccaggtgcc    1200
ctcaccacca atggcatcaa ccctgacacc agtactgaga tcggacgtgc taagaactgc    1260
cttagccctg aagacataat tgacaagtat aaagaggcga tttcctatta cagcaagtat    1320
aagaatgcgg gagtgattga gttggaagcg tgcatcaagg ctgtacgtgt ccttgcaatt    1380
cagaaacgga gcatggaagc atcagaattt cttcagaatg cagtttacat taaccttcga    1440
cagctttctg aggaagagaa aattcagcgc tacagcatcc tctccgagct ctatgagctg    1500
atcggcttcc atcgcaagtc tgcgttcttc aagcgcgtgg ccgccatgca gtgcgtggcc    1560
ccaagcatcc cggagcctgg gtggaggggcc tgctacaaac tcctcctgga aacgctgccc    1620
ggctacagtc tgtcgctgga tcccaaagat ttcagcagag gcacgcacag aggctgggct    1680
gcggtccaga tgcgtttgct ccatgaattg gtctacgcct cccgaaggat ggggaaccct    1740
gccctctctg tcagacacct gtccttcctt ctacagacca tgctggactt cttgtcggat    1800
```

```
caggaaaaga aagatgtggc ccaaagccta gagaactata cgtccaagtg tcctgggacc    1860
atggagccca tcgccctccc tggcggcctc accctgccac cggtgccctt caccaagctt    1920
cccgtcgtca ggcatgtgaa actattgaac cttcctgcta gcctccggcc acacaaaatg    1980
aaaagcttgc tgggtcagaa cgtgtcaacc aaaagtcctt tcatctattc accaattatc    2040
gcacacaacc gtggagaaga gcggaacaag aaaatagatt tccagtgggt tcaaggagat    2100
gtgtgtgaag ttcagctgat ggtatataac ccaatgccgt ttgaacttcg agttgaaaac    2160
atggggctgc tcaccagcgg agtggagttc gagtctctcc ctgcggcgct ttctcttccg    2220
gctgaatctg gtctgtaccc agtgacgctc gtcggggtcc cgcagacgac tggaacgatt    2280
actgtgaacg gttaccatac cacggtcttc ggtgtgttca gtgactgttt gctggataac    2340
ctgccgggaa taaaaccag tggctccaca gtggaagtca ttcccgcgtt gccaagactg    2400
cagatcagca cctctctgcc cagatctgca cattcattgc aaccttcttc tggtgatgaa    2460
atatctacta atgtatctgt ccagctttac aatggagaaa gtcagcaact aatcattaaa    2520
ttggaaaata ttggaatgga accattggag aaactggagg tcacctcgaa agttctcacc    2580
actaaagaaa aattgtatgg cgacttcttg agctggaagc tagaggaaac ccttgcccag    2640
ttccctttgc agcctgggaa ggtggccacg ttcacaatca acatcaaagt gaagctggat    2700
ttctcctgcc aggagaatct cctgcaggat ctcagtgatg atggaatcag tgtgagtggc    2760
tttccctgt ccagtccttt tcggcaggtc gttcggcccc gagtggaggg caaacctgtg    2820
aacccacccg agagcaacaa agcaggcgac tacagccacg tgaagaccct ggaagctgtc    2880
ctgaatttca atactctgg aggcccgggc cacactgaag gatattacag gaatctctcc    2940
ctggggctgc atgtagaagt cgagccgtct gtatttttca cccgagtcag caccctccca    3000
gcaaccagta cccggcagtg tcacctgctc ctggatgtct tcaactccac cgagcatgag    3060
ctgaccgtca gcaccaggag cagcgaggca ctcatcctgc acgccggcga gtgccagcga    3120
atggctattc aagtggacaa gttcaacttt gagagtttcc cggagtcccc tggggagaag    3180
gggcaatttg caaaccccaa gcagctggag aagagcggc gggaagcccg aggcctggag    3240
atccacagca agctgggcat ctgctggaga atcccctccc tgaagcgcag tggcgaggcg    3300
agtgtggaag gactcctgaa ccagctcgtc ctggagcacc tgcagctggc gcctctgcag    3360
tgggatgtgc tggtggacgg acagccatgt gaccgcgagg ctgtggcggc ctgccaggtg    3420
ggcgaccccg tgcgcctgga ggtgcggctg accaaccgga gcccgcgcag cgtagggccc    3480
ttcgccctca ctgtggtccc cttccaggac caccagaacg cgtgcacaa ctacgacctg    3540
cacgacaccg tctccttcgt gggctccagc accttctacc tcgacgcggt gcagccgtcc    3600
ggccagtcgg cctgcctcgg ggccctcctc ttcctctaca cgggagactt cttcctccac    3660
atccggttcc acgaggacag caccagcaag gagctgccac cctcttggtt ctgcctgccc    3720
agtgtgcacg tgtgtgccct ggaggcgcag gcctgagccc gcctacttcc gtccctcttt    3780
ctgcagggcc agaggtgacc ctgcctggcc tcccacaccc cctgcaatga gcaaggcctt    3840
cactgcagcc ccatctcctc ctcctccccc agaccctcc cagccctctc ctcctgttcc    3900
tcctgtagca tcttgctgg gctacgcaga agccccggac atggcagccc caccccatgc    3960
cacgccctt cctacactgt tccctggacc atacacaggc tgaagcagag gaaatcccaa    4020
agcgggtgcc catccagccc aggtcccagg atccctgcac ccatttctgt gacctggggc    4080
cccagccgtg ctgtgctgct catcccagca gagggacctc cctcgtccag cgacttccct    4140
ttggccatag aaagaaatgg tgagcatgag actgggcaca gcctgagggc gtgggcagct    4200
```

-continued

```
tcccaccctc cctgggcctt ggaatccccc aaggctggtt ttcttcctgg agaccccat   4260 gggcaacttg gcaggagaga tggtgccgta ggaggtcgtg gatggttgat gccaagagag   4320
gccctccacc cgtggtgggc aaatgtccag gcctgggctg gcagcccagg gctgtttctg   4380
ggtgctccct ggccccaggg tggcgtctgg ttaccatggc tgtgtgtgtc catgtctgca   4440
agcagttctt caataaatgg cctgcctccc cc   4472
```

<210> SEQ ID NO 2
<211> LENGTH: 1246
<212> TYPE: PRT
<213> ORGANISM: Homo Sapiens

<400> SEQUENCE: 2

```
Met Val Pro Ala Gly Asp Gln Asp Arg Ala Pro His Arg Gly Lys Pro
1               5                   10                  15

Ala Gln Ala Gly Ala Arg Thr Ser Arg Ala Ser Arg Ala Leu Arg Ser
            20                  25                  30

Trp Arg Arg Ser Gln Ala Ala Arg Ala Thr Val Thr His Pro Arg Gly
        35                  40                  45

Gly His Asp Arg Gly Ser His Gly Gly Tyr Arg Glu Gly His Arg Gly
    50                  55                  60

Cys Arg Arg Asp Pro Gln Trp Ala Ser Ala Gly Pro Pro Leu Ser
65                  70                  75                  80

Phe Thr Glu Glu Val Lys Phe Glu Leu Arg Ala Leu Lys Asp Trp Asp
                85                  90                  95

Phe Lys Met Ser Val Pro Asp Tyr Met Gln Cys Ala Glu Asp His Gln
            100                 105                 110

Thr Leu Leu Val Val Val Gln Pro Val Gly Ile Val Ser Glu Glu Asn
        115                 120                 125

Phe Phe Arg Ile Tyr Lys Arg Ile Cys Ser Val Ser Gln Ile Ser Val
    130                 135                 140

Arg Asp Ser Gln Arg Val Leu Tyr Ile Arg Tyr Arg His His Tyr Pro
145                 150                 155                 160

Pro Glu Asn Asn Glu Trp Gly Asp Phe Gln Thr His Arg Lys Val Val
                165                 170                 175

Gly Leu Ile Thr Ile Thr Asp Cys Phe Ser Ala Lys Asp Trp Pro Gln
            180                 185                 190

Thr Phe Glu Lys Phe His Val Gln Lys Glu Ile Tyr Gly Ser Thr Leu
        195                 200                 205

Tyr Asp Ser Arg Leu Phe Val Phe Gly Leu Gln Gly Glu Ile Val Glu
    210                 215                 220

Gln Pro Arg Thr Asp Val Ala Phe Tyr Pro Asn Tyr Glu Asp Cys Gln
225                 230                 235                 240

Thr Val Glu Lys Arg Ile Glu Asp Phe Ile Glu Ser Leu Phe Ile Val
                245                 250                 255

Leu Glu Ser Lys Arg Leu Asp Arg Ala Thr Asp Lys Ser Gly Asp Lys
            260                 265                 270

Ile Pro Leu Leu Cys Val Pro Phe Glu Lys Lys Asp Phe Val Gly Leu
        275                 280                 285

Asp Thr Asp Ser Arg His Tyr Lys Lys Arg Cys Gln Gly Arg Met Arg
    290                 295                 300

Lys His Val Gly Asp Leu Cys Leu Gln Ala Gly Met Leu Gln Asp Ser
305                 310                 315                 320

Leu Val His Tyr His Met Ser Val Glu Leu Leu Arg Ser Val Asn Asp
                325                 330                 335
```

```
Phe Leu Trp Leu Gly Ala Ala Leu Glu Gly Leu Cys Ser Ala Ser Val
                340                 345                 350

Ile Tyr His Tyr Pro Gly Gly Thr Gly Gly Lys Ser Gly Ala Arg Arg
            355                 360                 365

Phe Gln Gly Ser Thr Leu Pro Ala Glu Ala Ala Asn Arg His Arg Pro
        370                 375                 380

Gly Ala Gln Glu Val Leu Ile Asp Pro Gly Ala Leu Thr Thr Asn Gly
385                 390                 395                 400

Ile Asn Pro Asp Thr Ser Thr Glu Ile Gly Arg Ala Lys Asn Cys Leu
                405                 410                 415

Ser Pro Glu Asp Ile Ile Asp Lys Tyr Lys Glu Ala Ile Ser Tyr Tyr
            420                 425                 430

Ser Lys Tyr Lys Asn Ala Gly Val Ile Glu Leu Glu Ala Cys Ile Lys
        435                 440                 445

Ala Val Arg Val Leu Ala Ile Gln Lys Arg Ser Met Glu Ala Ser Glu
450                 455                 460

Phe Leu Gln Asn Ala Val Tyr Ile Asn Leu Arg Gln Leu Ser Glu Glu
465                 470                 475                 480

Glu Lys Ile Gln Arg Tyr Ser Ile Leu Ser Glu Leu Tyr Glu Leu Ile
                485                 490                 495

Gly Phe His Arg Lys Ser Ala Phe Phe Lys Arg Val Ala Ala Met Gln
            500                 505                 510

Cys Val Ala Pro Ser Ile Ala Glu Pro Gly Trp Arg Ala Cys Tyr Lys
        515                 520                 525

Leu Leu Leu Glu Thr Leu Pro Gly Tyr Ser Leu Ser Leu Asp Pro Lys
530                 535                 540

Asp Phe Ser Arg Gly Thr His Arg Gly Trp Ala Ala Val Gln Met Arg
545                 550                 555                 560

Leu Leu His Glu Leu Val Tyr Ala Ser Arg Arg Met Gly Asn Pro Ala
                565                 570                 575

Leu Ser Val Arg His Leu Ser Phe Leu Leu Gln Thr Met Leu Asp Phe
            580                 585                 590

Leu Ser Asp Gln Glu Lys Lys Asp Val Ala Gln Ser Leu Glu Asn Tyr
        595                 600                 605

Thr Ser Lys Cys Pro Gly Thr Met Glu Pro Ile Ala Leu Pro Gly Gly
610                 615                 620

Leu Thr Leu Pro Pro Val Pro Phe Thr Lys Leu Pro Val Val Arg His
625                 630                 635                 640

Val Lys Leu Leu Asn Leu Pro Ala Ser Leu Arg Pro His Lys Met Lys
                645                 650                 655

Ser Leu Leu Gly Gln Asn Val Ser Thr Lys Ser Pro Phe Ile Tyr Ser
            660                 665                 670

Pro Ile Ile Ala His Asn Arg Gly Glu Arg Asn Lys Lys Ile Asp
        675                 680                 685

Phe Gln Trp Val Gln Gly Asp Val Cys Glu Val Gln Leu Met Val Tyr
690                 695                 700

Asn Pro Met Pro Phe Glu Leu Arg Val Glu Asn Met Gly Leu Leu Thr
705                 710                 715                 720

Ser Gly Val Glu Phe Glu Ser Leu Pro Ala Ala Leu Ser Leu Pro Ala
                725                 730                 735

Glu Ser Gly Leu Tyr Pro Val Thr Leu Val Gly Val Pro Gln Thr Thr
            740                 745                 750

Gly Thr Ile Thr Val Asn Gly Tyr His Thr Thr Val Phe Gly Val Phe
```

-continued

```
            755                 760                 765
Ser Asp Cys Leu Leu Asp Asn Leu Pro Gly Ile Lys Thr Ser Gly Ser
        770                 775                 780

Thr Val Glu Val Ile Pro Ala Leu Pro Arg Leu Gln Ile Ser Thr Ser
785                 790                 795                 800

Leu Pro Arg Ser Ala His Ser Leu Gln Pro Ser Ser Gly Asp Glu Ile
                805                 810                 815

Ser Thr Asn Val Ser Val Gln Leu Tyr Asn Gly Glu Ser Gln Gln Leu
        820                 825                 830

Ile Ile Lys Leu Glu Asn Ile Gly Met Glu Pro Leu Glu Lys Leu Glu
        835                 840                 845

Val Thr Ser Lys Val Leu Thr Thr Lys Glu Lys Leu Tyr Gly Asp Phe
850                 855                 860

Leu Ser Trp Lys Leu Glu Glu Thr Leu Ala Gln Phe Pro Leu Gln Pro
865                 870                 875                 880

Gly Lys Val Ala Thr Phe Thr Ile Asn Ile Lys Val Lys Leu Asp Phe
                885                 890                 895

Ser Cys Gln Glu Asn Leu Leu Gln Asp Leu Ser Asp Asp Gly Ile Ser
            900                 905                 910

Val Ser Gly Phe Pro Leu Ser Ser Pro Phe Arg Gln Val Val Arg Pro
        915                 920                 925

Arg Val Glu Gly Lys Pro Val Asn Pro Pro Glu Ser Asn Lys Ala Gly
930                 935                 940

Asp Tyr Ser His Val Lys Thr Leu Glu Ala Val Leu Asn Phe Lys Tyr
945                 950                 955                 960

Ser Gly Gly Pro Gly His Thr Glu Gly Tyr Tyr Arg Asn Leu Ser Leu
                965                 970                 975

Gly Leu His Val Glu Val Glu Pro Ser Val Phe Phe Thr Arg Val Ser
            980                 985                 990

Thr Leu Pro Ala Thr Ser Thr Arg Gln Cys His Leu Leu Leu Asp Val
        995                 1000                1005

Phe Asn Ser Thr Glu His Glu Leu Thr Val Ser Thr Arg Ser Ser
1010                1015                1020

Glu Ala Leu Ile Leu His Ala Gly Glu Cys Gln Arg Met Ala Ile
1025                1030                1035

Gln Val Asp Lys Phe Asn Phe Glu Ser Phe Pro Glu Ser Pro Gly
1040                1045                1050

Glu Lys Gly Gln Phe Ala Asn Pro Lys Gln Leu Glu Glu Glu Arg
1055                1060                1065

Arg Glu Ala Arg Gly Leu Glu Ile His Ser Lys Leu Gly Ile Cys
1070                1075                1080

Trp Arg Ile Pro Ser Leu Lys Arg Ser Gly Glu Ala Ser Val Glu
1085                1090                1095

Gly Leu Leu Asn Gln Leu Val Leu Glu His Leu Gln Leu Ala Pro
1100                1105                1110

Leu Gln Trp Asp Val Leu Val Asp Gly Gln Pro Cys Asp Arg Glu
1115                1120                1125

Ala Val Ala Ala Cys Gln Val Gly Asp Pro Val Arg Leu Glu Val
1130                1135                1140

Arg Leu Thr Asn Arg Ser Pro Arg Ser Val Gly Pro Phe Ala Leu
1145                1150                1155

Thr Val Val Pro Phe Gln Asp His Gln Asn Gly Val His Asn Tyr
1160                1165                1170
```

```
Asp Leu His Asp Thr Val Ser Phe Val Gly Ser Ser Thr Phe Tyr
    1175            1180                1185

Leu Asp Ala Val Gln Pro Ser Gly Gln Ser Ala Cys Leu Gly Ala
    1190            1195                1200

Leu Leu Phe Leu Tyr Thr Gly Asp Phe Phe Leu His Ile Arg Phe
    1205            1210                1215

His Glu Asp Ser Thr Ser Lys Glu Leu Pro Pro Ser Trp Phe Cys
    1220            1225                1230

Leu Pro Ser Val His Val Cys Ala Leu Glu Ala Gln Ala
    1235            1240                1245

<210> SEQ ID NO 3
<211> LENGTH: 4472
<212> TYPE: DNA
<213> ORGANISM: Artificial Sequence
<220> FEATURE:
<223> OTHER INFORMATION: Representative TRAPPC9 nucleic acid sequence
      encoding a truncated NIBP protein

<400> SEQUENCE: 3
aaagtcggga gtgccatggt gccagctggg gatcaagacc gcgcgccaca caggggaag      60 ccggcccagg ctggggctcg cacctcacgt gcctcccggg ccctgcgatc ctggaggcgc    120
tcccaggccg cgcgcgccac ggtcacccac ccacgtgggg ggcacgaccg tgggagtcac    180
ggggggtacc gtgagggtca caggggtgc cgcagggatc acagtgggc ttccgcgggg     240 cctccacccc tgagcttcac agaggaagtg aaatttgagc tgcgcgccct gaaggactgg    300
gacttcaaaa tgagcgtccc tgactacatg cagtgtgctg aggaccacca gacgctgctc    360
gtggtggtcc agcctgtggg catcgtctcc gaggagaact tcttcaggat ctataagagg    420
atttgctctg tgagtcagat cagcgtgcgg gactcccagc gagtcctcta catccgctac    480
aggcaccact acccacccga gaacaacgag tggggtgact ccagacccca ccgcaaagtc    540
gtgggcctca tcaccatcac agactgcttc tcggccaagg actggccaca gacctttgag    600
aagttccacg tgcagaagga gatctaccgg tccacactgt atgactcccg gctctttgtc    660
ttcgggctgc agggggagat cgtggagcag ccgcgcaccg acgtggcttt ctaccccaac    720
tacgaggact gccagacggt ggagaagaga atcgaggact tcatcgagtc actgttcatc    780
gtgctggagt ccaagcgtct ggacagagcc acagacaagt ctggggataa gatccccctt    840
ctctgtgtcc cgtttgagaa aaaggacttt gtaggactgg acacagacag cagacattac    900
aagaagcggt gccaaggccg catgcggaag cacgtggggg acctgtgcct gcaggcaggg    960
atgctgcagg actccctggt gcattaccac atgtcggtgg agctgctgcg ttctgtgaat   1020
gactttctgt ggcttggagc tgccctggaa ggattgtgtt cagcttctgt catctatcac   1080
tatcctggtg gaactggtgg gaagagtgga gctcggaggt tccagggcag cacccttcct   1140
gctgaagcag ccaatagaca ccggccaggg gcacaggaag ttctcattga tccaggtgcc   1200
ctcaccacca tggcatcaa ccctgacacc agtactgaga tcggacgtgc taagaactgc   1260
cttagccctg aagacataat tgacaagtat aaagaggcga tttcctatta cagcaagtat   1320
aagaatgcgg gagtgattga gttggaagcg tgcatcaagg ctgtacgtgt ccttgcaatt   1380
cagaaacgga gcatggaagc atcagaattt cttcagaatg cagtttacat taacctttga   1440
cagcttcctg aggaagagaa aattcagcgc tacagcatcc tctccgagct ctatgagctg   1500
atcggcttcc atcgcaagtc tgcgttcttc aagcgcgtgg ccgccatgca gtgcgtggcc   1560
ccaagcatcg cggagcctgg gtggagggcc tgctacaaac tcctcctgga aacgctgccc   1620
```

-continued

| | |
|---|---|
| ggctacagtc tgtcgctgga tcccaaagat ttcagcagag gcacgcacag aggctgggct | 1680 |
| gcggtccaga tgcgtttgct ccatgaattg gtctacgcct cccgaaggat ggggaaccct | 1740 |
| gccctctctg tcagacacct gtccttcctt ctacagacca tgctggactt cttgtcggat | 1800 |
| caggaaaaga aagatgtggc ccaaagccta gagaactata cgtccaagtg tcctgggacc | 1860 |
| atggagccca tcgccctccc tggcggcctc accctgccac cggtgcccctt caccaagctt | 1920 |
| cccgtcgtca ggcatgtgaa actattgaac cttcctgcta gcctccggcc acacaaaatg | 1980 |
| aaaagcttgc tgggtcagaa cgtgtcaacc aaaagtcctt tcatctattc accaattatc | 2040 |
| gcacacaacc gtggagaaga gcggaacaag aaaatagatt tccagtgggt tcaaggagat | 2100 |
| gtgtgtgaag ttcagctgat ggtatataac ccaatgccgt ttgaacttcg agttgaaaac | 2160 |
| atggggctgc tcaccagcgg agtggagttc gagtctctcc ctgcggcgct ttctcttccg | 2220 |
| gctgaatctg gtctgtaccc agtgacgctc gtcggggtcc cgcagacgac tggaacgatt | 2280 |
| actgtgaacg gttaccatac cacgtcttc ggtgtgttca gtgactgttt gctggataac | 2340 |
| ctgccgggaa taaaaaccag tggctccaca gtggaagtca ttcccgcgtt gccaagactg | 2400 |
| cagatcagca cctctctgcc cagatctgca cattcattgc aaccttcttc tggtgatgaa | 2460 |
| atatctacta atgtatctgt ccagctttac aatggagaaa gtcagcaact aatcattaaa | 2520 |
| ttggaaaata ttggaatgga accattggag aaactggagg tcacctcgaa agttctcacc | 2580 |
| actaaagaaa aattgtatgg cgacttcttg agctggaagc tagaggaaac ccttgcccag | 2640 |
| ttcccttttgc agcctgggaa ggtggccacg ttcacaatca acatcaaagt gaagctggat | 2700 |
| ttctcctgcc aggagaatct cctgcaggat ctcagtgatg atggaatcag tgtgagtggc | 2760 |
| tttcccctgt ccagtccttt tcggcaggtc gttcggcccc gagtggaggg caaacctgtg | 2820 |
| aacccacccg agagcaacaa agcaggcgac tacagccacg tgaagaccct ggaagctgtc | 2880 |
| ctgaatttca aatactctgg aggcccgggc cacactgaag gatattacag gaatctctcc | 2940 |
| ctggggctgc atgtagaagt cgagccgtct gtattttca cccgagtcag caccctccca | 3000 |
| gcaaccagta cccggcagtg tcacctgctc ctggatgtct tcaactccac cgagcatgag | 3060 |
| ctgaccgtca gcaccaggag cagcgaggca ctcatcctgc acgccggcga gtgccagcga | 3120 |
| atggctattc aagtggacaa gttcaacttt gagagtttcc cggagtcccc tggggagaag | 3180 |
| gggcaatttg caaaccccaa gcagctggag aagagcggc gggaagcccg aggcctggag | 3240 |
| atccacagca agctgggcat ctgctggaga atcccctccc tgaagcgcag tggcgaggcg | 3300 |
| agtgtggaag gactcctgaa ccagctcgtc ctggagcacc tgcagctggc gcctctgcag | 3360 |
| tgggatgtgc tggtggacgg acagccatgt gaccgcgagg ctgtggcggc tgccaggtg | 3420 |
| ggcgaccccg tgcgcctgga ggtgcggctg accaaccgga gcccgcgcag cgtagggccc | 3480 |
| ttcgccctca ctgtggtccc cttccaggac caccagaacg gcgtgcacaa ctacgacctg | 3540 |
| cacgacaccg tctccttcgt gggctccagc accttctacc tcgacgcggt gcagccgtcc | 3600 |
| ggccagtcgg cctgcctcgg ggccctcctc ttcctctaca cgggagactt cttcctccac | 3660 |
| atccggttcc acgaggacag caccagcaag gagctgccac cctcttggtt ctgcctgccc | 3720 |
| agtgtgcacg tgtgtgccct ggaggcgcag gcctgagccc gcctacttcc gtccctcttt | 3780 |
| ctgcagggcc agaggtgacc ctgcctggcc tcccacaccc cctgcaatga gcaaggcctt | 3840 |
| cactgcagcc ccatctcctc ctcctccccc agaccctcc cagccctctc ctcctgttcc | 3900 |
| tcctgtagca tcttttgctgg gctacgcaga agccccggac atggcagccc caccccatgc | 3960 |
| cacgccccctt cctacactgt tccctggacc atacacaggc tgaagcagag gaaatcccaa | 4020 |

```
agcgggtgcc catccagccc aggtcccagg atccctgcac ccatttctgt gacctggggc    4080
cccagccgtg ctgtgctgct catcccagca gagggacctc cctcgtccag cgacttccct    4140
ttggccatag aaagaaatgg tgagcatgag actgggcaca gcctgagggc gtgggcagct    4200
tcccaccctc cctgggcctt ggaatccccc aaggctggtt ttcttcctgg agacccccat    4260
gggcaacttg gcaggagaga tggtgccgta ggaggtcgtg gatggttgat gccaagagag    4320
gccctccacc cgtggtgggc aaatgtccag gcctgggctg gcagcccagg gctgtttctg    4380
ggtgctccct ggccccaggg tggcgtctgg ttaccatggc tgtgtgtgtc catgtctgca    4440
agcagttctt caataaatgg cctgcctccc cc                                  4472

<210> SEQ ID NO 4
<211> LENGTH: 27
<212> TYPE: DNA
<213> ORGANISM: Artificial Sequence
<220> FEATURE:
<223> OTHER INFORMATION: Representative nucleic acid sequence
<220> FEATURE:
<221> NAME/KEY: misc_feature
<222> LOCATION: (22)..(22)
<223> OTHER INFORMATION: n is c or t

<400> SEQUENCE: 4
aatgcagttt acattaacct tngacag                                         27
```

METHOD AND APPARATUS FOR PREDICTING SUSCEPTIBILITY TO A DEVELOPMENTAL DISORDER

This application is a 371 filing of International Patent Application PCT/CA2010/000448 filed Mar. 26, 2010, which claims the benefit of application No. 61/164,200 filed Mar. 27, 2009.

FIELD OF INVENTION

The present invention relates to a method and apparatus for predicting susceptibility to a developmental disorder. In particular, the present invention relates to a method and apparatus for predicting susceptibility to non-syndromic autosomal recessive mental retardation and autism by detecting the presence of genetic mutation in the TRAPPC9 gene (Trafficking Protein Particle Complex, Subunit 9) and its encoded protein, also known as NIBP (NIK- AND IKK-β-Binding Protein), and KIAA1882.

BACKGROUND OF THE INVENTION

Mental retardation (MR) is believed to occur with a prevalence of ~2% within the population. MR is significantly more frequent in males than in females, and for that reason it had been assumed that ~25% of severe cases were X-linked, however recent review of data suggests that X-linked mutations contribute to no more than 10% of cases (Ropers & Hamel, 2005). Very little, however, is currently known about autosomal non-syndromic forms of MR. Autosomal dominant MR tends to occur only sporadically, due to the decreased likelihood of patients to procreate. Autosomal recessive forms of non-syndromic MR (NS-ARMR) are believed to be more common, yet only 5 genes have been identified so far, including PRSS12 (MRT1 on 4q25-q26; Molinari et al, 2002), CRBN (MRT2A on 3p26.2; Higgins et al, 2004), and CC2D1A (MRT3 on 19q13.12; Basel-Vanagaite et al, 2006). A recent study, using homozygosity mapping in large consanguineous families from Iran, has identified a further 8 loci (MRT4-12; Najmabadi et al, 2007). From this study, the discovery of GRIK2 as the cause of MRT6 on 6q21 (Motzacker et al, 2007), and TUSC3 on 8q12 as the cause of MRT7 have recently been made (Garshasbi et al, 2008).

The contribution of genetic factors to autism is also well established, but the mode of genetic transmission is unclear. It is apparent, however, that autism is a complex non-Mendelian disorder, and it is anticipated that genetic heterogeneity and oligo/polygenic inheritance are involved. Several genome-wide linkage studies have been performed, implicating a number of chromosomes, including 7q, 16p, 19q and 11p (IMGSAC, 1998 & 2001; CLSA, 1999; Liu et al, 2001; AGP 2007), however no genes have been identified so far. Evidence from studies of overlap between autism and mental retardation syndromes, as well as a number of studies using cytogenetic aberrations, also genomic copy number variants inferred from microarray analysis, have now implicated a number of specific genes such as SHANK3, NLGN3 & 4, NRXN1, CNTNAP2, UBE3A, FMR1, MECP2 and others (see reviews by Abrahams & Geschwind, 2008; Sutcliffe 2008). However, only very recently, several groups have started exploring the hypothesis that at least a small proportion of autism may be inherited in an autosomal recessive mode. The recent paper by Morrow et al (2008), where several genes such as PCDH10 and DIA1 were mapped through the identification of large homozygous deletions in consanguineous families with autism from the Arabian peninsula, Turkey and Pakistan, is an example of some of the potential of such an approach. Identification of autosomal recessive genes for autism may lead to the identification of relevant etiological biological pathways, and potentially the identification of other genes from the same pathway that may contribute to autism, and possibly inherited in a non-Mendelian fashion.

There is a need in the art to identify genetic markers associated with mental retardation and autism. Further there is a need in the art to identify nucleotide sequences associated with mental retardation and autism. There is also a need in the art for new diagnostic assays for mental retardation and autism.

SUMMARY OF THE INVENTION

The present invention relates to gene mutations. More specifically, the present invention relates to gene mutations associated with mental retardation.

According to an embodiment of the present invention, there is provided a method of predicting susceptibility to a developmental disability in a human subject, comprising the steps of:
obtaining a genomic DNA sample from the human subject;
determining a) if the DNA sample from the subject encodes a mutated NIBP protein relative to SEQ ID NO: 2, wherein said mutated NIBP protein is truncated, or b) if the DNA sample from the subject encodes a mutated NIBP protein relative to SEQ ID NO: 2, said DNA comprising a deletion, insertion, translocation, point mutation, frameshift mutation, or combination thereof that results in a mutated NIBP protein defined by truncation of NIBP, a non-functional NIBP protein or one that comprises nonsense mutations relative to SEQ ID NO:2;
wherein the presence of the mutated NIBP protein or a nucleotide sequence encoding the mutated NIBP protein identifies the subject as susceptible to the developmental disability.

As can be appreciated, a person of skill in the art could practice a substantially similar method by screening the mRNA from a human subject. However, such a screening method is less preferred.

According to a further embodiment of the present invention, there is provided a method as described above and further comprising,
amplifying a nucleic acid sequence corresponding to the nucleotide sequence containing position 1438 of SEQ ID NO:1 using a first primer that binds upstream of said position and a second primer that binds downstream of said position;
detecting the presence or absence of a T nucleotide at the position corresponding to 1438 in SEQ ID NO:1; and
determining the genotype of the human subject at the position corresponding to 1438 in SEQ ID NO:1,
wherein a homozygote for the T nucleotide is predictive of the developmental disability and a heterozygote for the T nucleotide is a carrier of the developmental disability.

Similar methodology may be employed to screen subjects for any point mutation, missense mutation, deletion, insertion, translocation, frameshift mutation or the like which results in truncation of the NIBP protein as compared to SEQ ID NO:2. Similarly, nonsense mutations in TRAPPC9 gene which result in extraneous or unrelated addition of amino acid sequences can easily be determined by a person of skill in the art, with or without the need of programs to align a mutated NIBP protein to the wild-type NIBP protein as provided in SEQ ID NO:2. Typically, in such an alignment, a first portion of the NIBP protein will exhibit high identity (greater than 95% identity, preferably 99% or higher identity) to a portion of SEQ ID NO:2, whereas a second portion of the NIBP protein will exhibit little (for example, less than 20% identity, preferably less than 10% identity, more preferably less than 5% identity) or no identity when aligned using a basic alignment program as known in the art using default parameters. In separate embodiments, a mutation causing truncation or addition of extraneous or unrelated addition of amino acids occurs in exons 1, 2, 3, 4, 5, 6, 7, 8, 9, 10, 11, 12, 13, or 14, of the TRAPPC9 encoding gene. As we have described mutations in exons 14 and 7 which result in truncated NIBP proteins and correlate with developmental disorder phenotype, it is reasonable to conclude that any mutation in exons 1-14 that results in truncation or the addition of extraneous or unrelated amino acids in NIBP could serve as a diagnostic marker to identify subjects that are susceptible to a developmental disorder as described below.

In a further embodiment, there is provided a method of predicting susceptibility to a developmental disability in a human subject, comprising the steps of
obtaining a biological sample from the human subject that comprises NIBP protein or a mutant protein thereof;
optionally isolating protein from the sample;
exposing the protein to an antibody that recognizes and binds a portion of a polypeptide sequence that corresponds to position 476 to 1246 of SEQ ID NO. 2; and
detecting the presence of the antibody/polypeptide complex,
wherein the absence of binding between the antibody and the polypeptide is predictive of the developmental disability. A similar method may be employed for any NIBP truncation protein or mutant NIBP protein as described herein.

In still a further embodiment, there is provided a method of predicting susceptibility to a developmental disability in a human subject, comprising the steps of
obtaining a biological sample from the human subject that comprises NIBP protein or a mutant protein thereof;
optionally isolating protein from the sample;
exposing the protein to an antibody that recognizes and binds a portion of a polypeptide sequence that corresponds to positions 1 to 1246 of SEQ ID NO. 2, for example, but not limited to the N-terminal region; and
detecting the presence of the antibody/polypeptide complex,
determining if the antibody has bound to wild-type, truncated or mutant NIBP protein based on one or more characteristics thereof, for example, size, known or available epitopes, amino acid sequence, isoelectric point, hydrophilicity, hydrophobicity, ability to interact with known binding partners, activity or any other method known in the art. For example, but not wishing to be considered limiting, a truncated NIBP protein may migrate further during electrophoresis than its counterpart wild-type protein. Such differences can easily be identified by a person of skill in the art.

The present invention also contemplates combinations of the methods as described throughout the disclosure herein.

The present invention also contemplates a nucleic acid sequence or complement thereof which hybridizes to a nucleotide sequence encoding a mutant NIBP protein defined by truncation of TRAPPC9, a non-functional NIBP protein, one of reduced function, or one that comprises nonsense mutations relative to SEQ ID NO:2.

In an embodiment, the nucleic acid as described above, or complement thereof does not hybridize to SEQ ID NO:1 or a complement thereof. In a further embodiment, the nucleic acid comprises a contiguous nucleotide sequence of SEQ ID NO:3 and comprises position 1438 thereof, or a contiguous nucleotide sequence complementary thereto.

The nucleic acid sequence as described above may be any length, for example from about 7 nucleotides to 100 or more nucleotides, for example, but not limited to, a 7-mer, 10-mer, 15-mer, 20-mer, 25-mer-, 30-mer, 35-mer, 40-mer, 45-mer, 50-mer, 55-mer, 60-mer, 65-mer, 70-mer, 75-mer, 80-mer, 85-mer, 90-mer, 95-mer, and 100-mer nucleic acid sequence or any size therein between.

The present invention also provides a physical support or substrate comprising the nucleic acid as described above attached thereto. The physical support or substrate may be, for example, but not limited to, a DNA array, microarray, bead, plastic well, carrier protein, non-proteinaceous macromolecule or the like. In a preferred embodiment the nucleic acid is covalently attached to the physical support or substrate optionally via a linker. Any linker known in the art may be used.

According to an aspect of the present invention there is provided a method of predicting susceptibility to a developmental disability in a human subject, comprising the steps of: amplifying a nucleic acid sequence containing position 1438 of SEQ ID NO:1 using a first primer that binds upstream of said position and a second primer that binds downstream of said position; detecting the presence of a T nucleotide at position 1438 in SEQ ID NO:1; and determining the genotype of the human subject at position 1438 in SEQ ID NO:1 (which is position 1423 from first translated nucleotide), wherein a homozygote for the T nucleotide is predictive of the developmental disability and a heterozygote for the T nucleotide is a carrier of the developmental disability.

In one embodiment, the developmental disability is mental retardation or autism.

In another embodiment, the step of amplifying involves polymerase chain reaction.

According to another aspect of the invention, there is provided an oligonucleotide comprising a contiguous nucleic acid containing position 1438 of SEQ ID NO. 3 and complements thereof.

In one embodiment the oligonucleotide is selected from a group consisting of 7-mer, 10-mer, 15-mer, 20-mer, 25-mer, 30-mer, 35-mer, 40-mer, 45-mer, 50-mer, 55-mer, 60-mer, 65-mer, 70-mer, 75-mer, 80-mer, 85-mer, 90-mer, 95-mer, and 100-mer nucleic acid sequence or complements thereof. It is also contemplated that an oligonucleotide of a length in between any one of the values or more than 100 nucleotides is encompassed within the scope of the present invention.

According to a further aspect of the present invention, there is provided an oligonucleotide that is 90% identical, more preferably 91%, 92%, 93%, 94%, 95%, 96%, 97%, 98%, 99%, 99.5%, or 100% identical to a contiguous nucleotide sequence containing position 1438 of SEQ ID NO:3, or any other mutation in TRAPPC9 that results in a truncated or mutated NIBP protein.

According to another aspect of the invention, there is provided a method of predicting susceptibility to a developmental disability in a human subject, comprising the steps of: obtaining a sample from the human subject; isolating protein from the sample; exposing the protein to an antibody that recognizes a portion of a polypeptide sequence that corresponds to position 476 to 1246 of SEQ ID NO. 2; and detecting the presence of the antibody/polypeptide complex, wherein the absence of binding between the antibody and the polypeptide is predictive of the developmental disability. Further, the method may also employ a positive control step of exposing the protein to an antibody that recognizes a portion of a polypeptide that corresponds to positions 1 to 475, for example in exon 1, 2, 3, 4, 5 or 6.

In an embodiment, the developmental disability is mental retardation or autism.

According to further aspect of the present invention, there is provided an apparatus for detecting a nucleotide in a nucleic acid sequence. The apparatus comprising: a substrate; a first oligonucleotide bound to the substrate, the first oligonucleotide comprising a contiguous nucleic acid sequence complementary to SEQ ID NO. 3 containing position 1438 of the sequence, or a nucleic acid sequence at least 90% identical thereto.

In one embodiment, the apparatus further comprises a second oligonucleotide bound to the substrate, the second oligonucleotide comprising a contiguous nucleic acid sequence complementary to SEQ ID NO. 1 containing position 1438 of the sequence.

In an embodiment, the first oligonucleotide comprises a 25-mer contiguous nucleic acid sequence.

In another embodiment, the second oligonucleotide comprises a 25-mer contiguous nucleic acid sequence.

In a further embodiment, the first oligonucleotide comprises a 60-mer contiguous nucleic acid sequence.

In yet a further embodiment, the second oligonucleotide comprises a 60-mer contiguous nucleic acid sequence.

According to a further aspect of the present invention, there is provided a nucleic acid comprising a sequence selected from the group consisting of: a) a nucleic acid sequence comprising SEQ ID NO. 4; b) a complement of a nucleic acid sequence comprising SEQ ID NO. 4; c) a fragment of either a) or b); d) a nucleic acid sequence capable of hybridizing to any one of a), b) or c); and e) a nucleic acid sequence that exhibits greater than about 70% sequence identity with the nucleic acid defined in a), b) or c).

According to another aspect of the present invention, a method of predicting susceptibility to a developmental disability in a human subject, comprising the steps of isolating RNA from the subject; hybridizing an oligonucleotide comprising a contiguous nucleic acid of SEQ ID NO. 1 to the RNA; wherein the absence of RNA is predictive of the developmental disability.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a representative wild-type TRAPPC9 nucleic acid sequence (SEQ ID NO. 1) encoding NIBP;

FIG. 2 shows a representative wild-type NIBP protein sequence (SEQ ID NO. 2) encoded by TRAPPC9;

FIG. 3 shows a representative TRAPPC9 nucleic acid sequence (SEQ ID NO. 3) encoding a truncated NIBP protein; and FIG. 4 shows a representative nucleic acid sequence (SEQ ID NO. 4) of the present invention.

DETAILED DESCRIPTION OF THE INVENTION

The following description is of a preferred embodiment.

A truncating mutation in the TRAPPC9 gene on chromosome 8q24 has been identified that associates with the developmental disabilities: non-syndromic autosomal recessive mental retardation (NS-ARMR) and autism.

TRAPPC9 is a 23 exon gene that encodes a 1246 amino acid protein, NIK and IKKβ binding protein (NIBP). This protein is expressed at high levels in the muscle and kidney, and to a lesser extent in the brain, heart and placenta (Hu et al, 2005). Only isoform 1 of the gene is present in the brain (Hu et al, 2005). NIBP is involved in the NF-Kappa-β signaling pathway, and directly interacts with IKKβ and MAP3K14 (Hu et al, 2005). It is likely involved in both classical and alternative activation of the NF-Kappa-β signalling pathway (Hu et al, 2005). It potentially plays a role in neuronal differentiation, but this requires further investigation (Hu et al, 2005). It is expressed in the cell bodies and processes of neurons (Hu et al, 2005). NIBP contains one known conserved region originally identified in *Saccharomyces cerevisiae* called Trs120 (pfam08626; Sacher et al, 2000). It is known to function in ER to Golgi traffic (Sacher et al, 2000).

One mutation that causes the truncation of the NIBP protein resides at position 1438 of the nucleic acid sequence shown in SEQ ID NO. 1 (FIG. 1). The single nucleotide polymorphism at this position results in a thymidine (T), as shown in SEQ ID NO. 3 (FIG. 3) instead of the wild-type cytosine (C) ("the C allele"). For the purposes of present invention, this polymorphism will be referred to as the C1438T polymorphism. However, it is to be noted that the polymorphism is also termed C1423T in Mir et al., 2009 (The American Journal of Human Genetics 85, 1-7, December 11 which is hereby incorporated by reference) due to differences in numbering conventions when counting from the coding sequence of GenBank Accession number NM_031466. The presence of T at position 1438 of SEQ ID NO. 3 ("the T allele"), results in a termination codon, instead of the wild-type arginine in the amino acid sequence shown by SEQ ID NO. 2 (FIG. 2). The resulting truncated protein comprises 475 amino acids compared to the full-length protein, which is made up of 1246 amino acids.

It has been found that the T allele is inherited in an autosomal recessive manner. As a result, individuals heterozygous for the allele may be carriers of the allele without having the phenotype of the disorder. Identifying and counselling these individuals may limit or prevent the possible transmission of the recessive genotype onto offspring.

The sample obtained from a subject may comprise any biological sample from which genomic DNA may be isolated, for example, but not to be limited to a tissue sample, a sample of saliva, a cheek swab sample, blood, or other biological fluids that contain genomic DNA. In a preferred embodiment, which is not meant to be limiting in any manner, the sample is a blood sample. In another embodiment, RNA or mRNA is isolated from the subject.

The method of obtaining and analyzing DNA or RNA is not critical to the present invention and any method or methods may be used (e.g. Ausubel, et al. (eds), 1989, Current Protocols in Molecular Biology, Green Publishing Associates, Inc., and John Wiley & Sons, Inc., New York, at p. 2.10.3, or Maniatis et al., in Molecular Cloning (A Laboratory Manual), Cold Spring Harbor Laboratory, 1982, p. 387-389). For example, which is not to be considered limiting in any manner, DNA may be extracted using a non-enzymatic high-salt procedure (Lahiri and Nurnberger 1991). Alternatively, the DNA may be analyzed in situ. RNA can isolated, for example, by phenol chloroform extraction and analyzed using RT-PCR.

Genotyping of the C1438T marker (or any of the other markers as described herein) may be performed by any method known in the art, for example PCR, sequencing, ligation chain reaction (LCR) or any other standard method known in the art that may be used to determine SNPs (single nucleic acid polymorphisms). In an embodiment, which is not meant to be limiting in any manner, amplifying the nucleic acid sequence containing the C1438T marker and genotyping the same is performed by PCR analysis using appropriate primers, probes and PCR conditions.

In one embodiment, the step of amplifying the sequence containing the C1438T marker involves subjecting the nucleic acid sample to PCR, wherein the program for denaturing, annealing, amplifying is stored on a computer readable medium for execution by a microprocessor. The program causes a machine containing the samples to cycle through various temperatures for set periods of time. A similar or different machine comprising one or more programs may be employed to convert physical information, for example, but not limited to binding of nucleic acids or probes to target sequences, amplification or the like to a different state, such as electronic or otherwise, for example a signal that can be printed, displayed pictorially or digitized.

In a further embodiment, the restriction enzyme Taq I is used to detect the presence of the T allele at C1438T marker. Taq I recognizes the consensus sequence, T C G A, which corresponds to the wild-type sequence of the TRAPPC9 gene in the area of the polymorphism. The T allele will disrupt this consensus sequence and Taq I will not be able to cut the sequence. As such Taq I (or an isoschizomer of TaqI, or other restriction enzyme recognizing this or the complementary wild-type or mutated sequence) can be used to easily determine the genotype of the subject. Other methods also may be used.

An apparatus, such as microarray or DNA chip, can be used to detect the presence or absence of the C1438T marker or any other nucleic acid which results in a truncated NIBP protein or mutated NIBP protein as described herein. In this case, but without wishing to be limiting in any manner, an oligonucleotide may be bound to a substrate, which is suitable for this type of application. In an embodiment the oligonucleotide preferably comprises a contiguous nucleic acid, for example, the sequence from SEQ ID NO. 3 (FIG. 3) containing position 1438 of the sequence or a sequence substantially identical thereto. Another oligonucleotide can also be bound to the substrate. For example, but not wishing to be limiting, a nucleotide sequence comprising a complement of the nucleic acid sequence from SEQ ID NO:3 containing position 1438 of the sequence may be employed. In a further embodiment, the oligonucleotide comprises a contiguous nucleic acid sequence from SEQ ID NO. 1 containing position 1438 of the sequence, or a complement thereof or a sequence substantially identical thereto. In one embodiment the oligonucleotides are 7, 10, 12, 15, 16, 17, 19, 21, 23, 25 or more nucleotides in length. In another embodiment, the oligonucleotides are 60 nucleotides in length or more. Alternatively, the oligonucleotides may be defined by a range of any two of the values noted above or any two values therein between. A person skilled in the art will recognize that the length of the oligonucleotides can be altered based on the parameters of the assay. It is envisaged that the apparatus can contain other oligonucleotide sequences to confirm the subject's susceptibility to the developmental disability or to test for the susceptibility of additional diseases or disorders, comorbid or otherwise.

As noted above, the C1438T marker in TRAPPC9 gene, results in a truncation of the NIBP protein. In a separate study, sequence analysis also identified a 4 base pair deletion resulting in a frameshift and premature truncation: pLeu772TrpfsX7 in exon 14. This observation provides a unique opportunity to use the difference in protein length, between the wildtype and the truncation proteins, to predicted the susceptibility of a subject to a developmental disability.

As such, the present invention also contemplates screening methods which identify and/or characterize the proteins as defined above within biological samples from subjects. Such samples may or may not comprise DNA or RNA. For example, such screening or testing methods may employ immunological methods, for example, but not limited to antibody binding assays such as ELISAs or the like, protein sequencing, electrophoretic separations to identify the proteins as described above in a sample. As will be evident to a person of skill in the art, the screening methods allow for the differentiation of the proteins as defined herein from wild type proteins known in the art.

Also contemplated by the present invention is a nucleic acid comprising or consisting of a sequence selected from the group consisting of: a) a nucleic acid sequence comprising SEQ ID NO. 4 (FIG. 4); b) a complement of a nucleic acid sequence comprising SEQ ID NO. 4; c) a fragment of either a) or b); d) a nucleic acid sequence capable of hybridizing to any one of a), b) or c); and e) a nucleic acid sequence that exhibits greater than about 70% sequence identity with the nucleic acid defined in a), b) or c).

A nucleic acid sequence exhibiting at least 70% identity thereto is understood to include sequences that exhibit 70%, 75%, 80%, 85%, 90%, 91%, 92%, 93%, 94%, 95%, 96%, 97%, 98%, 99%, 99.9% or 100% identity, or an value therein between to SEQ ID NO. 4. Further, the nucleic acid may be defined as comprising a range of sequence identity as defined by any two of the values listed or any values therein between.

Any method known in the art may be used for determining the degree of identity between nucleic acid sequences. For example, but without wishing to be limiting, a sequence search method such as BLAST (Basic Local Alignment Search Tool: (Altschul S F, Gish W, Miller W, Myers E W, Lipman D J (1990) J Mol Biol 215: 403-410) can be used according to default parameters as described by Tatiana et al., FEMS Microbiol Lett. 174:247-250 (1990), or on the National Center for Biotechnology Information web page at ncbi.nlm.gov/BLAST/, for searching closely related sequences. BLAST is widely used in routine sequence alignment; modified BLAST algorithms such as Gapped BLAST, which allows gaps (either insertions or deletions) to be introduced into alignments, PSI-BLAST, a sensitive search for sequence homologs (Altschul et al., (1997) Nucleic Acid Res. 25:3389-3402); or FASTA, which is available on the world wide web at ExPASy (EMBL-European Bioinformatics Institute). Similar methods known in the art may be employed to compare DNA or RNA sequences to determine the degree of sequence identity.

Stringent hybridization conditions may be, for example but not limited to hybridization overnight (from about 16-20 hours) hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours); or hybridization in Church aqueous phosphate buffer (7% SDS; 0.5M NaPO$_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each for unique sequence regions.

Also contemplated by the present invention is a method of predicting susceptibility to a developmental disability in a human subject, comprising the steps of: isolating RNA from the subject; hybridizing an oligonucleotide comprising a contiguous nucleic acid of SEQ ID NO. 1 to the RNA; wherein the absence of RNA complementary to the oligonucleotide is predictive of the developmental disability.

The presence of the T allele at position 1438 of SEQ ID NO. 4 is believed to lead to nonsense-mediated RNA decay, and hence reduction or total loss of the mRNA. This presents a unique opportunity to detect the presence of TRAPPC9 mRNA in a subject for the purposes of predicting the susceptibility of the subject to a developmental disorder.

The present invention will be further illustrated in the following examples. However it is to be understood that these examples are for illustrative purposes only, and should not be used to limit the scope of the present invention in any manner.

EXAMPLE 1

The family in which the C1438T mutation was identified, MR-2019, is a large family with multiple incidences of consanguinity between first cousins. We obtained the DNA of 8 affected and 12 unaffected family members.

Affymetrix 5.0 SNP microarray analysis was conducted to identify genetic differences between the affected and unaffected family members. The results were analyzed with dChip, using homozygosity mapping as a basis for identifying regions of susceptibility. A 3.2 Mb region of autozygosity was identified in the family at locus 8q24, from 139,465,102-142,726,810 (UCSC March 2006 Build), consisting of a run of 606 consecutive homozygous SNPs. This region overlaps with a 6.8 Mb locus identified in an Iranian NS-ARMR pedigree (Najmabadi et al, 2007).

The 3.2 Mb region contains 12 genes, only one of which has been previously implicated in MR. This gene, KCNK9 (MIM 605874), has been shown to be causal in recently identified Birk-Barel Syndrome (Barel et al, 2008) (MIM 612292). KCNK9 was sequenced and found to be normal in the family used in this example.

Additional genes in the region were sequenced that appeared to be good candidates for MR based on functional and expression data obtained from the UCSC database. An expression-based algorithm was used to identify genes in our region that co-expressed with known causal MR genes (genome.ucla.edu/projects/UGET). A mutation in TRAPPC9 was identified. The mutation, at C1438T causes the gene to be truncated at the end of its 7th exon. Each of the 8 affected individuals were homozygous for the T allele, whereas all of the 12 unaffected individuals were either homozygous for the C allele or carriers of the T allele.

The present invention has been described with regard to one or more embodiments. However, it will be apparent to persons skilled in the art that a number of variations and modifications can be made without departing from the scope of the invention as defined in the claims.

REFERENCES

All citations are hereby incorporated by reference.

Abrahams B S, Geschwind D H. (2008). Advances in autism genetics: on the threshold of a new neurobiology. Nat Rev Genet 9:341-355.

AGP Consortium (2007). Mapping autism risk loci using genetic linkage and chromosomal rearrangements Barel, O., Shalev, S. A., Ofir, R., Cohen, A., Zlotogora, J., Shorer, Z., et al. (2008). Maternally inherited birk barel mental retardation dysmorphism syndrome caused by a mutation in the genomically imprinted potassium channel KCNK9. American Journal of Human Genetics, 83(2), 193-199.

Basel-Vanagaite, L.; Attia, R.; Yahav, M.; Ferland, R. J.; Anteki, L.; Walsh, C. A.; Olender, T.; Straussberg, R.; Magal, N.; Taub, E.; Drasinover, V.; Alkelai, A.; Bercovich, D.; Rechavi, G.; Simon, A. J.; Shohat, M. (2006). The CC2D1A, a member of a new gene family with C2 domains, is involved in autosomal recessive non-syndromic mental retardation. J. Med. Genet. 43:203-210

Collaborative Linkage Study of Autism (1999) An autosomal genomic screen for autism. Am J Med Genet (Neuropsych Genet) 88:609-615.

Garshasbi M, Hadavi V, Habibi H, Kahrizi K, Kariminejad R, Behjati F, Tzschach A, Najmabadi H, Ropers H H, Kuss A W. (2008) A defect in the TUSC3 gene is associated with autosomal recessive mental retardation. Am J Hum Genet 82:1158-1164.

Higgins, J. J.; Pucilowska, J.; Lombardi, R. Q.; Rooney, J. P. (2004). A mutation in a novel ATP-dependent Lon protease gene in a kindred with mild mental retardation. Neurology 63:1927-1931.

Hu, W. H., Pendergast, J. S., Mo, X. M., Brambilla, R., Bracchi-Ricard, V., Li, F., et al. (2005). NIBP, a novel NIK and IKK(beta)-binding protein that enhances NF-(kappa)B activation. The Journal of Biological Chemistry, 280(32), 29233-29241.

International Molecular Genetic Study of Autism Consortium (1998) A full genome screen for autism with evidence for linkage to a region on chromosome 7q. Hum Mol Genet 7: 571-578.

International Molecular Genetic Study of Autism Consortium (2001) A genomewide screen for autism: strong evidence for linkage to chromosomes 2q, 7q, and 16p. Am J Hum Genet 69:570-581.

Liu J, Nyholt D R, Magnussen P, Parano E, Pavone P, Geschwind D, Lord C, Iversen P, Hoh J, Ott J, Gilliam T C; Autism Genetic Resource Exchange Consortium. (2001). A genomewide screen for autism susceptibility loci. Am J Hum Genet 69:327-340

Molinari, F.; Rio, M.; Meskenaite, V.; Encha-Razavi, F.; Auge, J.; Bacq, D.; Briault, S.; Vekemans, M.; Munnich, A.; Attie-Bitach, T.; Sonderegger, P.; Colleaux, L. (2002). Truncating neurotrypsin mutation in autosomal recessive nonsyndromic mental retardation. Science 298:1779-1781.

Morrow E M, Yoo S Y, Flavell S W, Kim T K, Lin Y, Hill R S, Mukaddes N M, Balkhy S, Gascon G, Hashmi A, Al-Saad S, Ware J, Joseph R M, Greenblatt R, Gleason D, Ertelt J A, Apse K A, Bodell A, Partlow J N, Barry B, Yao H, Markianos K, Ferland R J, Greenberg M E, Walsh C A (2008) Identifying autism loci and genes by tracing recent shared ancestry. Science. 321:218-223.

Motazacker M M, Rost B R, Hucho T, Garshasbi M, Kahrizi K, Ullmann R, Abedini S S, Nieh S E, Amini S H, Goswami C, Tzschach A, Jensen L R, Schmitz D, Ropers H H, Najmabadi H, Kuss A W. (2007) A defect in the ionotropic glutamate receptor 6 gene (GRIK2) is associated with autosomal recessive mental retardation. Am J Hum Genet 81:792-798.

Najmabadi H, Motazacker M M, Garshasbi M, Kahrizi K, Tzschach A, Chen W, Behjati F, Hadavi V, Nieh S E, Abedini S S, Vazifehmand R, Firouzabadi S G, Jamali P, Falah M, Seifati S M, Gruters A, Lenzner S, Jensen L R, Ruschendorf F, Kuss A W, Ropers H H: (2007) Homozygosity mapping in consanguineous families reveals extreme heterogeneity of non-syndromic autosomal recessive mental retardation and identifies 8 novel gene loci. Hum Genet 121:43-48

Ropers H H, Hamel B C. (2005) X-linked mental retardation. Nat Rev Genet 6:46-57.

Sacher, M., Barrowman, J., Schieltz, D., Yates, J. R., 3rd, & Ferro-Novick, S. (2000). Identification and characterization of five new subunits of TRAPP. European Journal of Cell Biology, 79(2), 71-80.

Sutcliffe J S (2008) Genetics. Insights into the pathogenesis of autism. Science 321:208-209

I claim:

1. An isolated protein defined by truncation of SEQ ID NO:2 at position 475.

2. A method of predicting susceptibility to a developmental disability in a human subject, comprising the steps of:
   obtaining a genomic DNA sample from the human subject; and
   determining whether the DNA sample from the subject encodes a protein according to claim 1; by
   amplifying a nucleic acid sequence corresponding to the nucleotide sequence containing position 1438 of SEQ ID NO:1 using a first primer that binds upstream of said position and a second primer that binds downstream of said position;
   detecting the presence of a T nucleotide at the position corresponding to 1438 in SEQ ID NO: 1;
   and determining the genotype of the human subject at the position corresponding to 1438 in SEQ ID NO: 1,
   wherein a homozygote for the T nucleotide is predictive of the developmental disability and a heterozygote for the T nucleotide is a carrier of the developmental disability.

3. The method of claim 2, wherein the developmental disability is mental retardation or autism.

4. The method of claim 2, wherein the step of amplifying involves polymerase chain reaction.

* * * * *

UNITED STATES PATENT AND TRADEMARK OFFICE
CERTIFICATE OF CORRECTION

PATENT NO. : 8,716,444 B2  
APPLICATION NO. : 13/258929  
DATED : May 6, 2014  
INVENTOR(S) : John B. Vincent Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 51 days.

Signed and Sealed this

Twenty-ninth Day of September, 2015

Michelle K. Lee  
*Director of the United States Patent and Trademark Office*